US008323926B2

(12) United States Patent
Kang et al.

(10) Patent No.: US 8,323,926 B2
(45) Date of Patent: Dec. 4, 2012

(54) **GENE FROM *HANCENULA POLYMORPHA* CAPABLE OF CONTROLLING UNFOLDED PROTEIN RESPONSE AND METHOD FOR INCREASING EFFECT OF SECRETION USING THE SAME**

(75) Inventors: Hyun Ah Kang, Daejeon (KR); Hye-Yun Moon, Daejeon (KR); Doo-Byoung Oh, Daejeon (KR); Sang Ki Rhee, Seoul (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 425 days.

(21) Appl. No.: 12/304,354

(22) PCT Filed: Jun. 13, 2007

(86) PCT No.: PCT/KR2007/002853
§ 371 (c)(1),
(2), (4) Date: Jan. 30, 2009

(87) PCT Pub. No.: WO2007/145467
PCT Pub. Date: Dec. 21, 2007

(65) Prior Publication Data
US 2010/0297694 A1    Nov. 25, 2010

(30) Foreign Application Priority Data

Jun. 16, 2006    (KR) .................... 10-2006-0054557

(51) Int. Cl.
| C12P 21/06 | (2006.01) |
| C12N 15/00 | (2006.01) |
| C12N 1/00 | (2006.01) |
| C07H 21/04 | (2006.01) |
| C07K 1/00 | (2006.01) |

(52) U.S. Cl. ............... 435/69.1; 435/320.1; 435/254.11; 536/23.7; 530/350

(58) Field of Classification Search ........................ None
See application file for complete search history.

(56) References Cited

U.S. PATENT DOCUMENTS
2004/0170622 A1    9/2004    Glimcher et al.
2004/0186070 A1 *  9/2004    Penttila et al. .................. 514/44

FOREIGN PATENT DOCUMENTS
WO    WO 00/29429 A2    5/2000

OTHER PUBLICATIONS

Kang et al., "Genome-Wide Analysis of Transcriptional Responses to Secretion Stress in the Methylotrophic Yeast *Hansenula polymorpha*", International Meeting of the Federation of Korean Microbiological Societies, Oct. 2006, pp. 89-90.*

Merriam-Webster online dictionary definition of "represent", obtained from www.merriam-webster.com, last viewed on Sep. 13, 2010, 2 pages.*
Oh et al. "Fabrication of a Partial Genome Microarray of the Methylotrophic Yeast *Hansenula polymorpha*: Optimization and Evaluation of Transcript Profiling", J. Microbiol. Biotechnol. 14:1239-1248, 2004.*
Merriam-Webster online dictionary definition of "represent", last viewed on Nov. 23, 2010, 1 page.*
NCBI revision history for GenBank Accession No. DQ679915, Apr. 19, 2011, 1 page.*
Oldenburg et al, "Recombination-Mediated PCR-Directed Plasmid Construction In Vivo in Yeast," Nucleic Acids Research, (1997) vol. 25, p. 451-452.
Travers et al, "Functional and Genomic Analyses Reveal an Essential Coordination between the Unfolded Protein Response and ER-Associated Degradation," Cell, 2000, 101, p. 249-258.
Ruegsegger et al, "Block of HAC1 mRNA Translation by Long-Range Base Pairing Is Released by Cytoplasmic Splicing upon Induction of the Unfolded Protein Response," Cell, 2001, 107, p. 103-114.
Calfon et al, "IRE1 couples endoplasmic reticulum load to secretory capacity by processing the XBP-1 mRNA," Nature, 2002, 415, p. 92.
Ramezani-Rad et al, "The *Hansenula polymorpha* (strain CBS4732) genome sequencing and analysis," FEMS Yeast Res., 2003, 4, 207-5.
Levine et al, "Isolation and Characterization of a Thermotolerant Methanol-Utilizing Yeast," Appl. Microbiol.,(1973) vol. 26, 982-990.
Welihinda A.A. et al, US Gene Expr. "The cellular response to protein misfolding in the endoplasmic reticulum" 1999, vol. 7 (4-6) 293-300.
Valkonen M. et al, FI Appl Environ Microbiol, "Effects of inactivation and constitutive expression of the unfolded-protein response pathways on protein production in the yeast *Saccharomyces cerevisiae*" Apr. 2003, vol. 69(4) 2065-2072.
Sybirna K et al, FR Curr Genet "A new *Hansenula polymorpha* HAP4 homologue which contains only the N-terminal conserved domain of the protein is fully functional in *Saccharomyces cerevisiae*" Mar. 2005, vol. 47(3): 172-181.
Schroder M, et al, US "The unfolded protein response represses differentiation through the RPD3-SIN3 histone deacetylase" Embo J., Jun. 2, 2004, vol. 23(11), 2281-2292.

* cited by examiner

*Primary Examiner* — David J Steadman
(74) *Attorney, Agent, or Firm* — Casimir Jones, S.C.

(57) ABSTRACT

The present invention relates to a novel *H. polymorpha* gene regulating Unfolded Protein Response (UPR) and a method for improving the efficiency of secretory expression of a recombinant protein using the same, more particularly, a method for improving the efficiency of secretory expression of a recombinant protein by identifying, modifying, and optimizing the HpHAC1 gene, which encodes a key transcription regulatory factor of the UPR mechanism in *H. polymorpha*, and a regulatory mechanism mediated by the gene. According to the present invention, the secretory expression system of *H. polymorpha* can be used for the mass-production of secretory proteins for industrial and medical applications, thereby producing a large amount of the proteins at low cost. Accordingly, the method is employed in the production of the proteins for industrial and medical use, so as to reduce economic burden for a patient, and contribute to the improvement in the welfare of all mankind.

9 Claims, 8 Drawing Sheets

[Figure 1] SEQ ID NO:1 a)

```
atgactgctc tcaacagctc tgtccagcac caagaagtct cttcggactt ggcttttgga   61
actctacctc caagaaagtg tgccaagacc gaagaggaga aagagcaaag aagagttgaa  121
agaatcttga gaaacagaag ggcagctcac gcgtctagag aaaagaagag aagacatgtt  181
gagtaactgg aaaactatgt gactgatctg gagtctgcgc tggcgacaca tgagggcaat  241
tatcggaaga tggccaaaat tcaatcgagc ctgatatctc tgtcgtctga acatggaatc  301
gattactcgt ctgtggattt agctgttgaa ccatgtccta aagttgaaag acggaaggt  361
ttggagttga ctggttcaat tcagtgaaa aaacagaaaa tcgcctggc gaaatcgccc  421
aaatcgttat cgagaaaatc gaagtcggaa atcccatcac caagttttga tgagaatatt  481
ttttctgagg aggaaaaga acatgacgat ggtattgagg aatacgggaa agcaggacaa  541
gaagcaacg aggctccatc cttgtctcac aaccgcaaaa gaaggcgca agatgcttat  601
atctcgcctc cggctccac ctccccatcc aagttgaacc ttgaagaga cgaaaggatc  651
tcaaacatg aatacagtaa ctgtttgat gacaccgatg acattttcc gtggagaag  721
tcatcaagtc tcgagctgta taaacaggat gatctgacca tggcatcatt tgtgaaacaa  781
gaagaggaag aaatggtgcc atttgtgaaa caggaagacg agttcaagtt tcctgattcg  841
ggtttcaacg ctgacgttg tcatcttatc caagtggaag acctctgctc ttttaatagc  901
gtgcatcatc cagcagtgct gattgtgaag ttatgaaaa ctcaatgtt tgaagcgatt  961
cagtcgaact aacttgaaat gagactcgtt ttttgggtat ttgtttgaca gtctcatctc 1021
aagtatcgt atcagttatt tcgttatctt gtgctctgct tctacctcgct ttaattgtta 1081
agttcgtcag cagcaccatt aacagcagat agtatcgaca accactttga atttgcagca 1141
ccattaacag cagagagtat cgacaaccac tttgaatttg acgactattt gtcttga     1201
``` b)

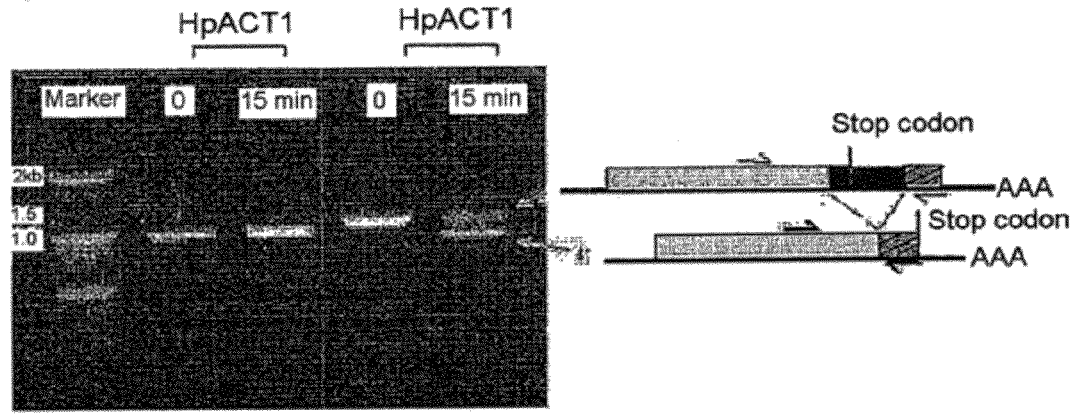

[Figure 2]
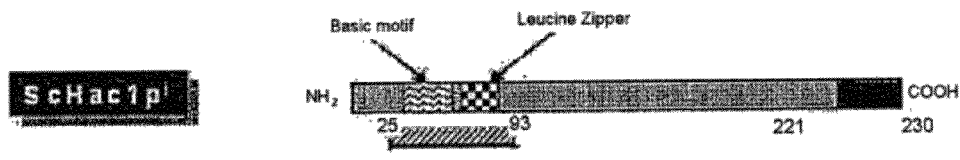

[Figure 3]
a)
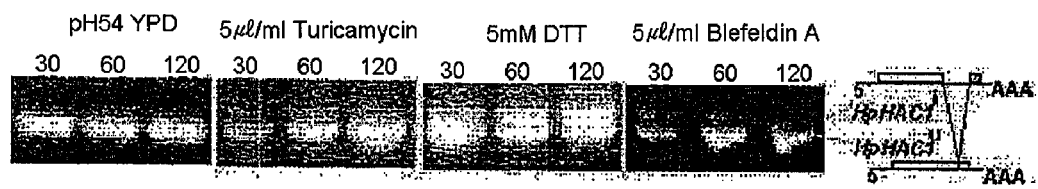
b)
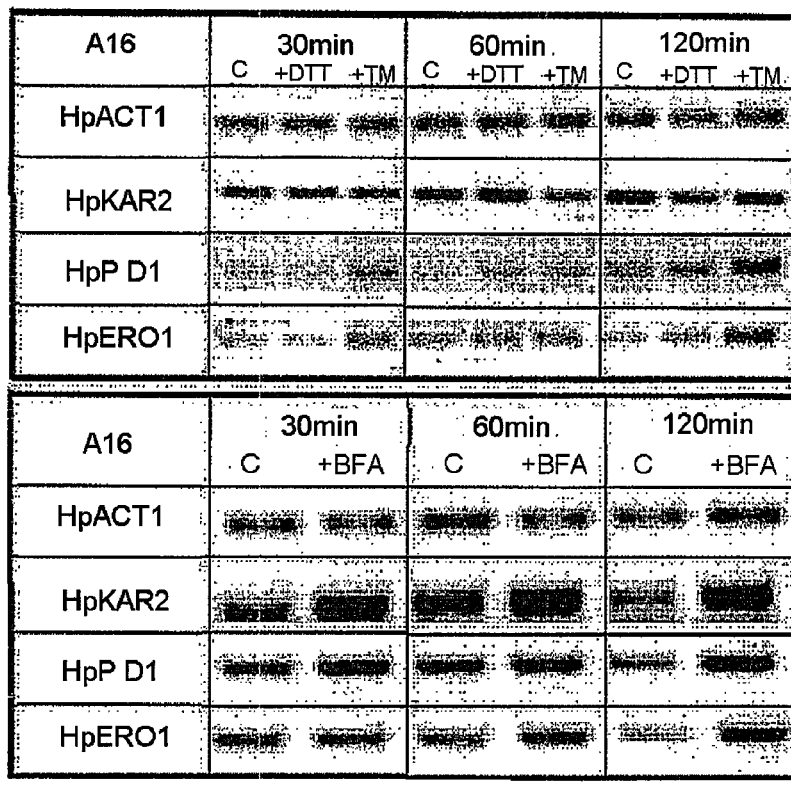

[Figure 4]
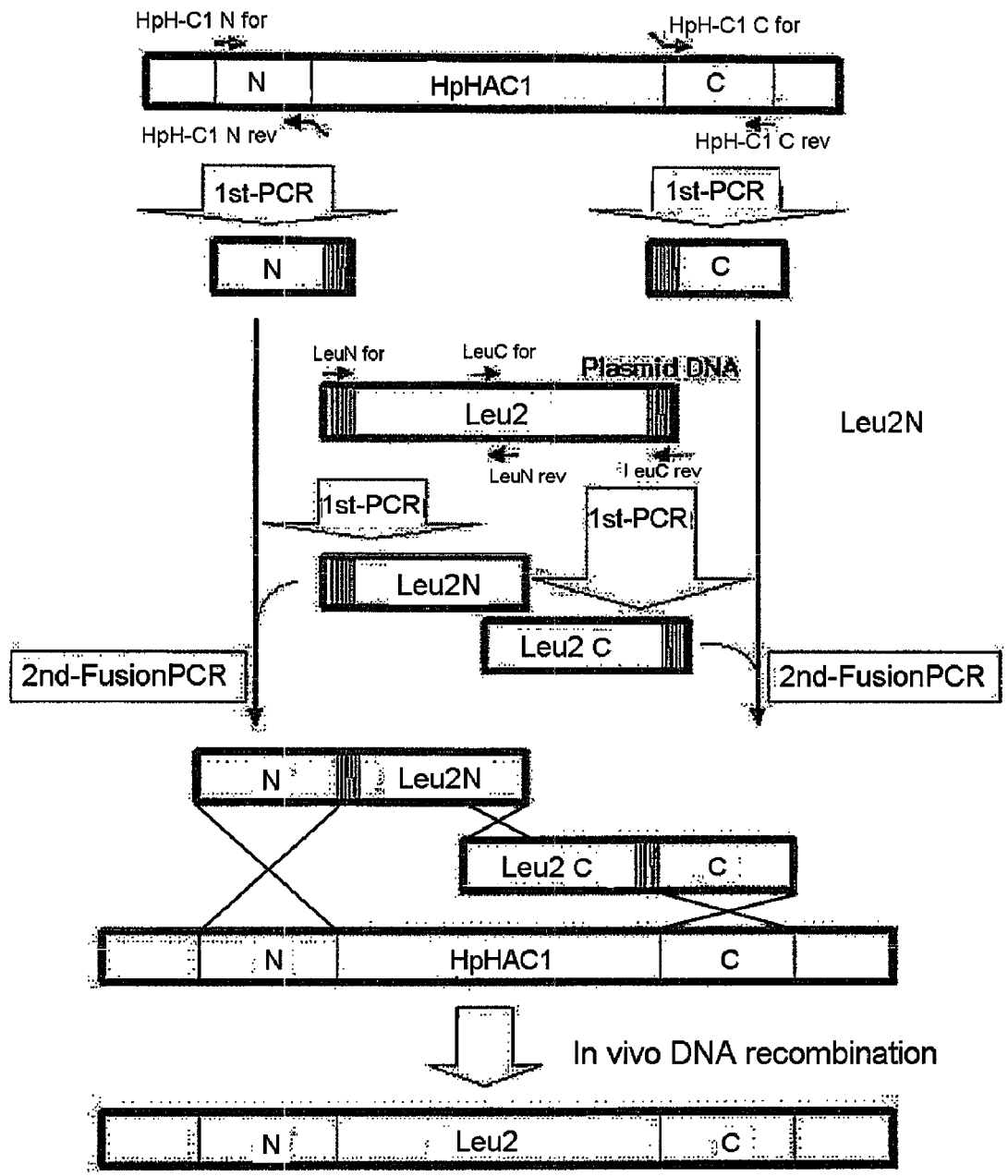

[Figure 5]
a)
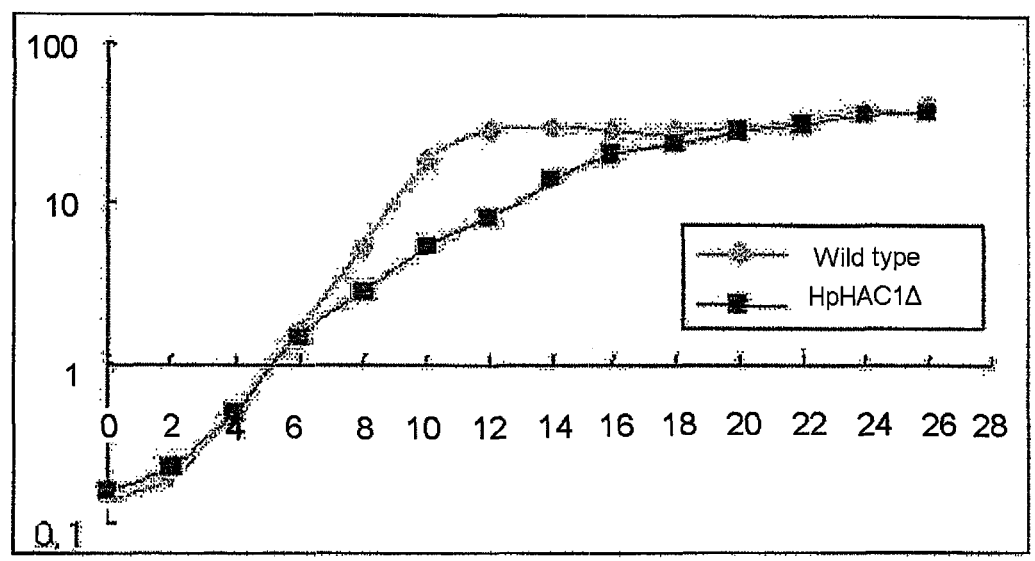
b)
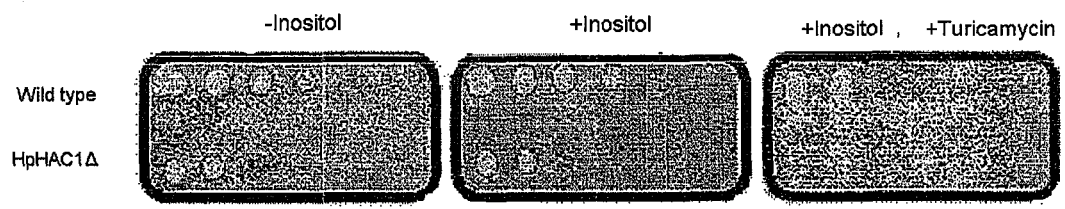

[Figure 6]
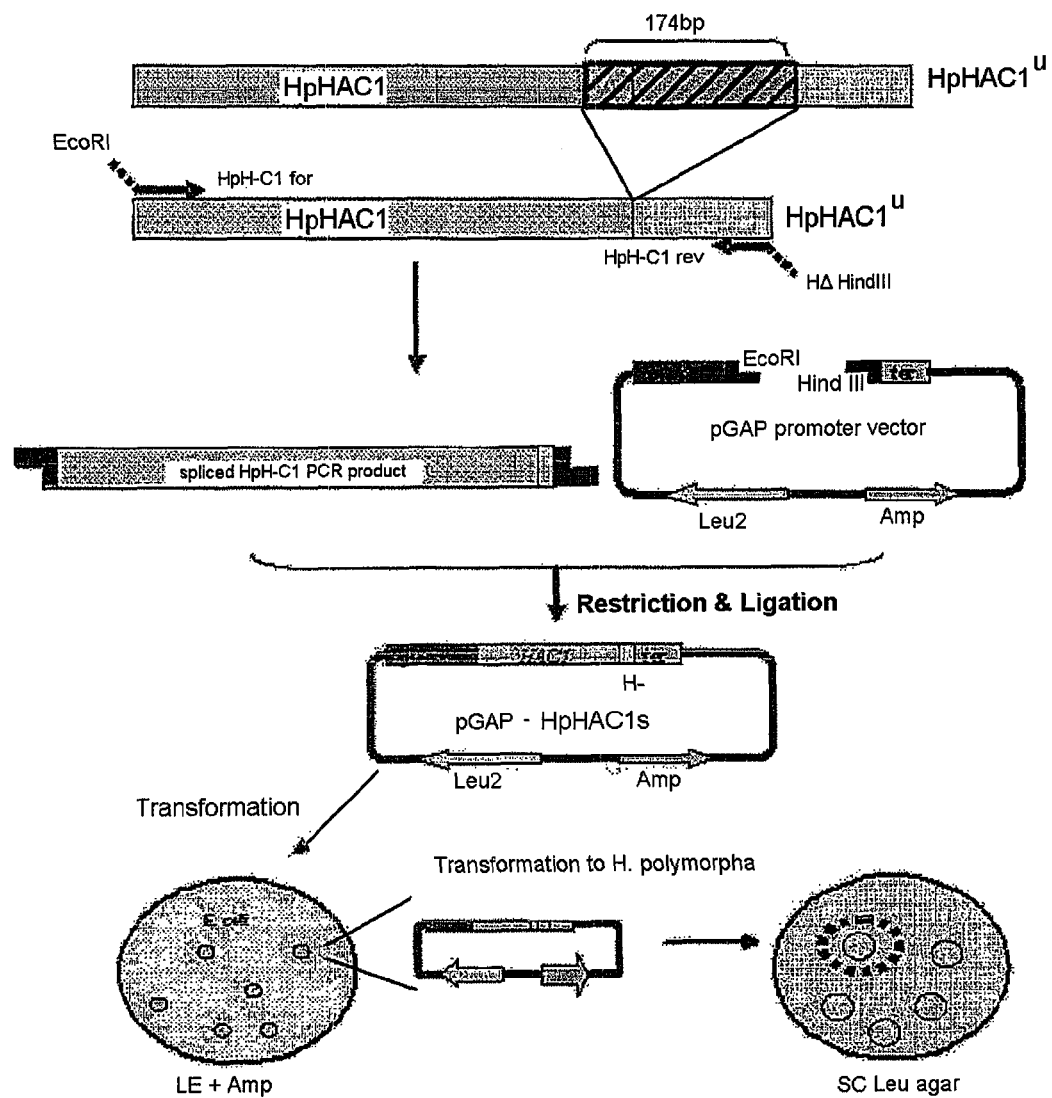

[Figure 7]
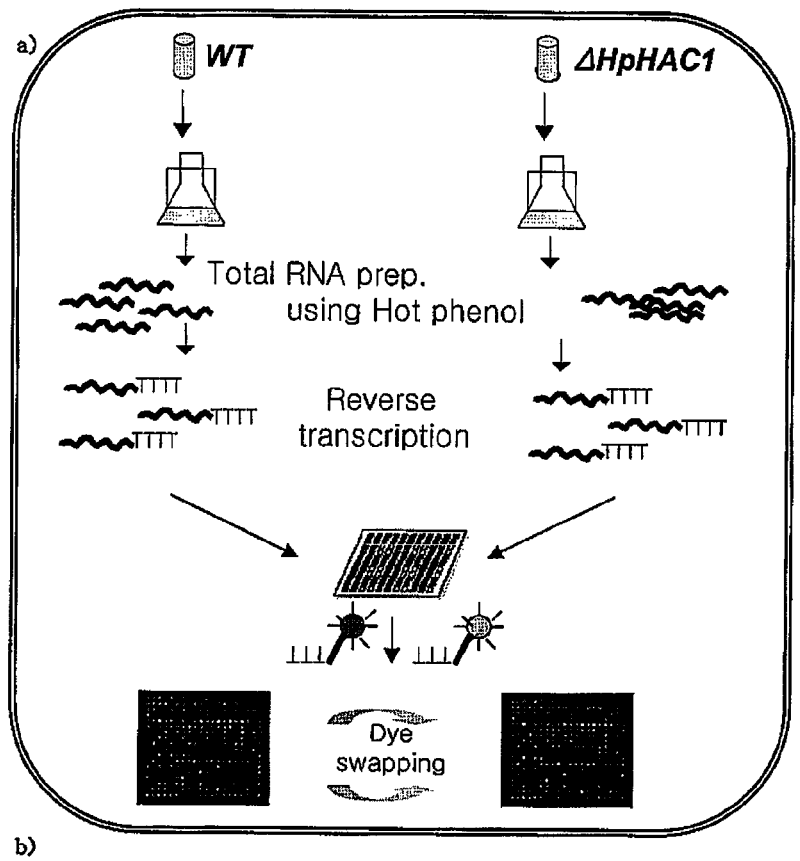
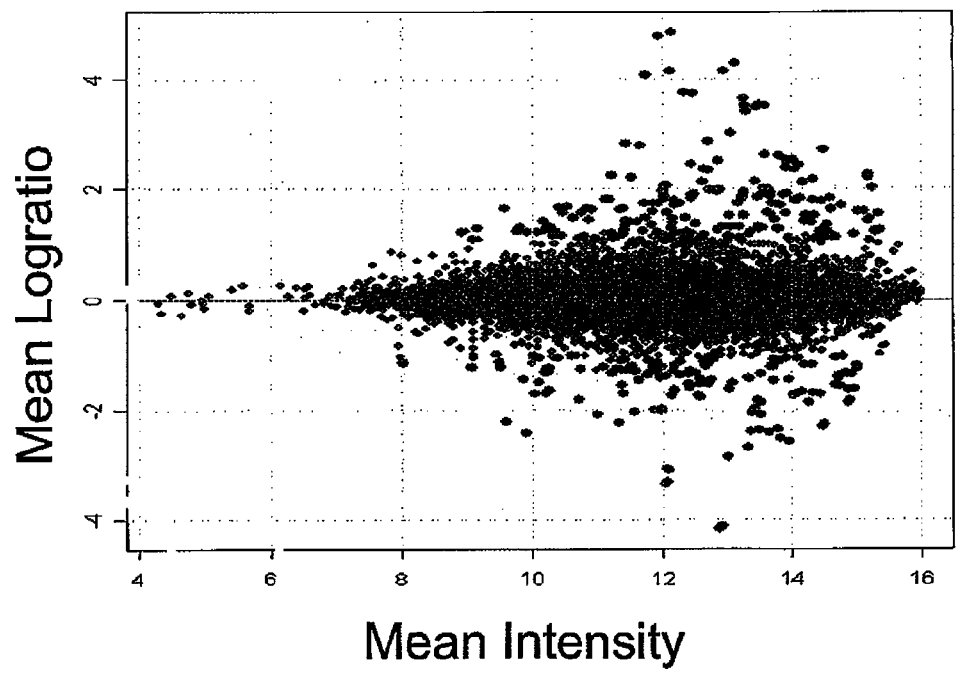

[Figure 8]
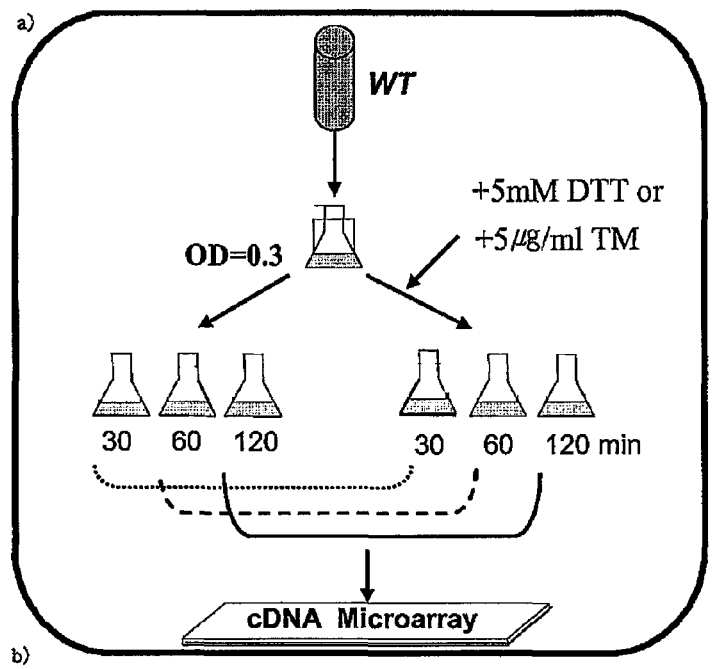
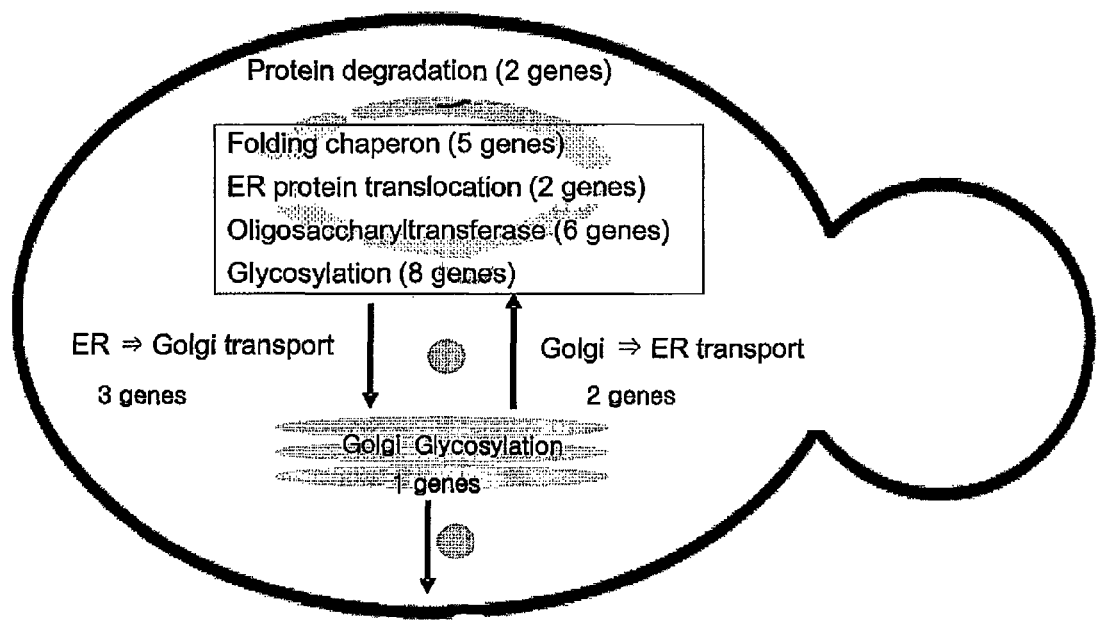

GENE FROM *HANCENULA POLYMORPHA* CAPABLE OF CONTROLLING UNFOLDED PROTEIN RESPONSE AND METHOD FOR INCREASING EFFECT OF SECRETION USING THE SAME

TECHNICAL FIELD

The present invention relates to a novel gene of *Hansenula polymorpha* (*H. polymorpha*) controlling Unfolded Protein Response (UPR) and a method for improving the efficiency of secretory expression of recombinant proteins using the same gene, more particularly, a method for improving the efficiency of secretory expression of recombinant proteins by identifying, modifying, and optimizing the HpHAC1 gene, which encodes a key regulatory factor of UPR in *H. polymorpha*, and by elucidating the HpHAC1-mediated regulatory mechanism.

BACKGROUND ART

All eukaryotic cells including yeast have an intracellular organelle called the endoplasmic reticulum (ER) which is responsible for the transport of secretory proteins and membrane proteins. That is, secretory proteins to be transported to the outside of the cell not to cytoplasm are translated in ribosomes, and immediately translocated into the ER. In this secretory pathway, the misfolded proteins are accumulated to generate ER stress, which leads to activate a stress response mechanism, UPR, in order to remove the generated ER stress (or secretion stress). UPR has been found in all eukaryotic cells, from a unicellular eukaryotic microorganism, yeast, to the highest eukaryotic organism, human.

The study at the genome level on the UPR mechanism of yeast was carried out with the traditional yeast *Saccharomyces cerevisiae* (*S. cerevisiae*) in the 2000s (Cell 101, 249, 2000), which resulted in the identification of underlying regulatory and action mechanisms of UPR (Cell 107, 103, 2001; Nature 415, 92, 2002).

The UPR in yeast was first shown to be mainly regulated by a regulatory transcription factor, Hac1p, which is encoded by the HAC1 gene in *S. cerevisiae*. However, subsequently, studies on the UPR mechanism in higher organisms have been more actively conducted, leading to the discovery of a variety of regulatory factor such as ATF6 and PERK proteins, in addition to XBP1 protein corresponding to the mammalian homolog of Hac1p.

Yeast, as a unicellular eukaryotic microorganism, has the same intracellular organelles as do higher eukaryotic organisms, and their secretion mechanisms are quite similar each other. Therefore, yeast has been considered as an excellent recombinant protein expression host, in which proteins derived from human can be easily expressed at low cost.

In an animal cell expression system, there is an advantage of expressing complex glycoproteins derived from human. However, the main drawbacks to the system include low productivity, high cost, and a long period of time to develop its cell lines. Moreover, a risk of virus and prion contamination is problematic, since animal cells are very similar to human cells. In contrast, yeast can be a more practical expression system, in that it can easily produce the desired recombinant proteins at lower cost and it has been exploited by Mankind for thousands of years in fermentation process. Currently, several yeast strains possess GRAS (generally recognized as safe) status.

Among various yeast species, the traditional yeast *S. cerevisiae* has been a subject of biological study, and developed as a host for the production of recombinant proteins. However, *S. cerevisiae* has lower capacity for the secretory production of functionally active proteins for industrial use, as compared to other industrial yeasts such as *Pichia pastoris* or *H. polymorpha*. Accordingly, instead of *S. cerevisiae*, these non-*Saccharomyces* yeasts become increasingly used as a host for secretory expression.

The methylotrophic yeast *H. polymorpha* has recently attracted a great deal of interest as a host having excellent ability in secretory expression of recombinant proteins. A great deal of success using *H. polymorpha* expression systems has been reported in the production of phytase (13.5 g/L), and hepatitis B vaccine for medical use. In particular, the mass-production of hepatitis B vaccine was achieved due to the economical advantage of *H. polymorpha* as a production host, so that the recombinant vaccines at cheap price could be supplied to many third world countries, contributing to the improvement in the welfare of all mankind.

*H. polymorpha* has been internationally recognized as an excellent host system for mass-production of recombinant proteins for industrial and medical applications, and thus the development of recombinant protein production technologies using *H. polymorpha* is highly expected to be very useful in the field of biotechnology. Accordingly, in industry and market, there is a need to develop *H. polymorpha* as a host system that efficiently produces high quality of secretory proteins, including glycoproteins derived from human, by improving its ability of expressing and secreting recombinant proteins.

The present inventors have performed basic and applied researches to develop *H. polymorpha* as a host for secretory expression of recombinant proteins for the past ten years, and recently developed a whole-genome microarray system to analyze the regulatory mechanisms of *H. polymorpha* at a genome level. In an effort to up-grade a cell remodeling technique for optimizing the ability of secretory expression in *H. polymorpha*, we have isolated a *H. polymorpha* HAC1 gene (HpHAC1), which encodes an important regulatory transcription factor involved in UPR, and developed the deletion and overexpression strains thereof, so as to analyze their characteristics. Further, the inventors have performed a microarray analysis for them, so as to provide a basis for understanding a UPR mechanism that relieves the secretion stress, and a method for optimizing the ability of secretory expression in *H. polymorpha*, thereby completing the present invention.

DISCLOSURE

Technical Problem

It is an object of the present invention to provide a protein having an activity to increase the expression of genes involved in the response to relieve the secretion stress, in which the protein has an amino acid sequence represented by SEQ ID NO: 3 or an amino acid sequence having 90% or more homology therewith.

It is another object of the present invention to provide a nucleic acid encoding the protein, preferably comprising a nucleic acid sequence thereof represented by SEQ ID NO: 2 or represented by SEQ ID NO:1, which is a precursor of SEQ ID NO: 2 before the splicing specific to this gene or fragments of SEQ ID NO:1.

It is still another object of the present invention to provide a recombinant vector comprising a nucleic acid encoding the protein having an activity to increase the expression of the genes involved in the response to relieve the unfolded protein stress, in which the protein has an amino acid sequence represented by SEQ ID NO: 3 or an amino acid sequence having 90% or more homology therewith.

It is still another object of the present invention to provide an *E. coli* host cell transformed with the recombinant vector.

It is still another object of the present invention to provide a *H. polymorpha* host cell transformed with the recombinant vector.

It is still another object of the present invention to provide *H. polymorpha* mutant strains having the reduced Unfolded Protein Response, which can be obtained by deletion or mutation of the HpHAC1 gene coding for a novel transcription factor increasing the expression of the genes involved in the response to relieve the unfolded protein stress.

It is still another object of the present invention to develop a production host showing good cell growth, in which the HpHAC1 gene is constantly expressed.

It is still another object of the present invention to provide a method for preparing the production host having the improved ability of secretory expression of recombinant proteins, in which the HpHAC1 gene is constantly expressed or overexpressed.

DESCRIPTION OF DRAWINGS

FIG. 1A illustrates a nucleic acid sequence of the HpHAC1 gene of *H. polymorpha*, and FIG. 1B illustrates the reverse transcriptase-polymerase chain reaction (RT-PCR) analysis for the spliced HpHAC1 gene and its diagram. The product of RT-PCR was separated according to the size by electrophoresis on an agarose gel, and the nucleic acid sequence of the fragment which are reduced in size by splicing was analyzed to confirm the HAC1 specific splicing site, which was underlined (FIG. 1A). Each stop codon before and after the splicing, which was changed by splicing, was shown in bold.

FIG. 2A is a diagram showing the result of amino acid sequence analysis of *H. polymorpha* and *S. cerevisiae* HAC1 proteins, and FIG. 2B is the diagram of domains showing high homology between two yeast HAC1 proteins.

FIGS. 3A and B show the results of exploring the induction conditions for a secretion stress relief response, UPR (unfolded protein response) in *H. polymorpha*. FIG. 3A is the result of analyzing the conditions based on the splicing status of HpHAC1 mRNA, and FIG. 3B is the result of analyzing the change of the expression level of *H. polymorpha* genes (HpKAR2, HpPDI1, HpERO1) corresponding to UPR target genes known in *S. cerevisiae*. A wild-type *H. polymorpha* strain was cultivated up to exponential growth phase, treated with the optimal concentrations of 5 ug/ml tunicamycin, 5 mM DTT (Dithiothreitol), and Blefeldin A for 30 minutes, 60 minutes, and 120 minutes, and then harvested for the experiments.

FIG. 4 is a diagram showing the process of fusion PCR and in vivo DNA recombination in order to delete the HpHAC1 gene in *H. polymorpha*.

FIG. 5A is a drawing showing the result of analyzing the growth characteristics of the *H. polymorpha* wild-type and an HpHAC1 deletion mutant (Hphac1Δ) strains. In liquid culture, two strains were initially inoculated at an OD600 of 0.1, and the OD600 was measured at every 2 hours. Further, the culture media, in which two strains were in exponential growth phase, were successively diluted by 10-fold dilutions, and 2 μl of each diluted samples were spotted on minimal solid media supplemented with inositol only, with inositol and tunicamycin together, respectively, and incubated for 2 additional days to analyze their growth characteristics (FIG. 5B).

FIG. 6 is a diagram showing the process of developing a cell line overexpressing the HpHac1 protein. The spliced HpHAC1 mRNA was amplified by RT-PCR, and cloned into an expression vector for *H. polymorpha* by genetic recombination technique to construct a pGAP-HpHAC1s vector. Further, the vector was transformed with a *H. polymorpha* strain to prepare an HpHac1 overexpression strain.

FIGS. 7A and B are drawings showing the process and the result of analyzing the whole genome expression profiles of the wild-type *H. polymorpha* and the Hphac1Δ mutant strains in exponential growth phase (OD600=0.5), which were analyzed by DNA microarray experiments. FIG. 7A is a diagram showing the overall experimental design for the microarray experiments, and FIG. 7B is a scatter plot comparing the differences in the expression of each gene.

FIGS. 8A and 8B are diagrams showing the result of screening the UPR target genes regulated by the HpHac1 protein (HpHac1p) by two sets of microarray experiments. FIG. 8A is a diagram showing the design for two sets of microarray experiments, and FIG. 8B is a diagram showing the number of the UPR target genes regulated by HpHAC1, which was screened by the microarray experiments, and classified according to the function of secretory expression in yeast.

BEST MODE

The present invention relates to a cell reconstruction technique to increase the productivity of recombinant proteins, by optimizing protein secretory expression in *H. polymorpha*, which is actively used as a host for the production of recombinant proteins.

In all eukaryotic cells, proteins to be secreted outside are cotranslationally transported into the ER, in which the proteins undergo their folding and modification. Therefore, in the case of the secretion of a large amount of over-expressed recombinant proteins using an overexpression promoter or the like, an excessive amount of recombinant proteins causes the ER stress due to the overloaded capacity of proteins involved in folding and modification. The incorrect proteins, which are not properly folded or modified due to overexpression, are accumulated in the ER, which generates stress in a cell and leads to inhibition of cell growth or cell apoptosis.

If the incorrect proteins, which are not properly folded or modified, are accumulated in the ER, secretion stress is generated, which activates a counter mechanism called UPR (unfolded protein response) to relieve secretion stress.

In a conventional yeast, *S. cerevisiae*, a membrane protein encoded by IRE1 (Ire1p) mainly recognizes the proteins incorrectly folded, and its nuclease activity is activated, so that the HAC1 precursor mRNA, known as a sole substrate of Ire1p, can be cleaved. The cleated HAC1 mRNA is ligated by tRNA ligase, and, eventually, this HAC1 specific splicing leads to generate the active HAC1 protein by translation.

The present inventors identified the HpHAC1 gene in a *H. polymorpha* DL-1 strain, based on genomic information of a methylotrophic yeast, *H. polymorpha* (Levine and Cooney, Appl. Microbiol., 26, 982-990), and discovered that the gene also undergoes a splicing mechanism specific to HAC1 during secretion stress. A nucleic acid sequence of the spliced and activated HpHAC1 mRNA was represented by SEQ ID NO: 2, and a nucleic acid sequence of the precursor mRNA was represented by SEQ ID NO: 1.

In one embodiment, the present invention provides a protein having an activity of increasing the expression of the target genes involved in the UPR pathway, in which the protein has the amino acid sequence represented by SEQ ID NO: 3 or the amino acid sequence having 90% or more homology therewith.

In general, since the precursor mRNA of the HAC1 gene has a secondary structure that inhibits a translation process, only the splicing process by Ire1p can lead to the translation of HAC1 mRNA. Accordingly, the amino acid sequence of HpHac1p was determined by the nucleic acid sequence after the splicing, and then the expressed HpHac1p has a transcription factor activity to increase the expression of a gene family in the UPR pathway. The amino acid sequence of HpHac1p having a transcription factor activity described by the present invention is represented by SEQ ID NO: 3.

According to the present invention, the transcription factor HpHac1p of *H. polymorpha* was found to have the amino acid sequence represented by SEQ ID NO: 3, which is resulted from the splicing being specific to HAC1. Further, the protein was shown to increase the expression of target genes involved in the UPR pathway by microarray experiments described in Example 5. Therefore, as long as a protein has an activity of increasing the expression of UPR target genes, a protein and fragment thereof having 90% homology with HpHac1p are included in the present invention.

As used herein, the term "homology" refers to the degree of similarity with an amino acid sequence of a wild-type, and the present invention comprises an amino acid sequence having preferably 75% or more homology with the amino acid sequence encoding the HpHAC1 protein of the present invention, more preferably 85% or more, even more preferably 90% or more, and most preferably 95% or more. The comparison of homology was performed with the naked eye or with sequence comparison programs that are commercially available. The commercially available computer programs can calculate the homology percentage (%) between two or more sequences, and the homology (%) may be calculated over contiguous sequences.

As used herein, the phrase "UPR target gene" indicates a gene whose expression is increased in order to relieve secretion stress response in the ER, which includes genes increasing secretion efficiency by assisting protein folding and modification in the ER. Preferably, it includes a gene family identified by the microarray experiments in Example 5.

In another embodiment, the present invention provides nucleic acid sequence encoding the protein.

A nucleic acid encoding the HpHAC1 protein has preferably a nucleic acid sequence represented by SEQ ID NO: 1 or 2. SEQ ID NO: 1 represents an inactive precursor mRNA, which is changed to mRNA represented by SEQ ID NO: 2 by cleavage and ligation, called as slicing, upon secretion stress. The present inventors deposited the HpHAC1 gene of *H. polymorpha* having a nucleic acid sequence represented by SEQ ID NO: 2, which is translated into the active protein, in GenBank (Deposit No. DQ679915). Further, a recombinant vector pGAP-HpHAC1s comprising the gene was prepared, transformed into *E. coli* DH5α strain (*E. coli*), and deposited at KCTC (Korean Collection for Type Cultures, Korea Institute of Bioscience and Biotechnology, 52, Ueun-dong, Yusung-gu, Daejeon-si, Korea) on Jun. 13, 2006 (Deposit No. KCTC10960BP).

In still another embodiment, the present invention provides a recombinant vector comprising a nucleic acid encoding the protein, which has a transcription factor activity increasing the expression of UPR target genes, and the amino acid sequence represented by SEQ ID NO: 3 or amino acid sequence having 90% or more homology therewith.

The recombinant vector comprises preferably a nucleic acid sequence encoding the protein, which has a transcription factor activity increasing the expression of UPR target genes, and the amino acid sequence represented by SEQ ID NO: 3 or amino acid sequence having 90% or more homology therewith.

As used herein, the term "vector" refers to any conventional means used for introducing DNA into a host cell, and includes the conventional vectors such as plasmid vector, cosmid vector, bacteriophage vector, and virus vector.

The preferred vector includes regulatory elements for gene expression such as promoter, initiation codon, stop codon, polyadenylation signal, and enhancer, as well as signal sequences or leader sequences for membrane targeting or secretion, and a variety of vectors can be prepared according to the purpose.

In still another embodiment, the present invention provides an *E. coli* host cell transformed by the recombinant vector, preferably a transformed host cell deposited with Deposit No. KCTC10960BP.

Further, the present inventors prepared a transformed host, in which the HpHAC1 protein is constantly expressed by introducing the recombinant vector into *H. polymorpha*. The host is characterized in that its secretory expression ability is improved by the overexpressed UPR target genes due to constant expression of the HpHAC1 protein.

In still another embodiment, the present invention provides a *H. polymorpha* host cell transformed by the recombinant vector.

The present inventors prepared a *H. polymorpha* mutant strain (HpHac1Δ), in which the HpHAC1 gene is deleted in order to understand the mechanism of UPR response to relieve the secretion stress in *H. polymorpha*. A method for specifically inactivating only a target gene on a genome can be performed by methods established in the related art, but are not limited thereto.

In the present invention, in order to specifically delete the HpHAC1 gene, a fusion PCR method and in vivo homologous recombination method can be employed. *H. polymorpha* was transformed with a vector containing a selectable marker between 5'-terminus and 3'-terminus of HpHAC1 gene, so as to induce homologous recombination of the genome and the vector.

In still another embodiment, the present invention provides a *H. polymorpha* mutant strain having reduced UPR, in which HpHAC1 gene is deleted or mutated.

When the HpHac1Δ strain constructed according to the invention was cultivated in a conventional complex media, YPD, the growth of the Hphac1Δ strain was found to be greatly delayed from the late exponential growth phase to the stationary growth phase, as compared to the wild-type strain (FIG. 5A). Such characteristic is particular to *H. polymorpha*, since other yeast strains with HAC1 deletion have been reported not to have any apparent growth defective phynotypes in complex media. Further, the HAC1 deletion mutant strain of conventional yeast cannot grow without inositol, that is, they are inositol auxotrophs. However, the *H. polymorpha* Hphac1Δ strain is not an inositol auxotroph (FIG. 5B). It was found that the growth of Hphac1Δ strain was delayed on solid media, regardless of the presence of inositol. Further, in the case of culturing on solid media containing tunicamycin, which is a material inducing secretion stress by inhibiting N-linked glycosylation of glycoprotein, the growth of Hphac1Δ strain was found to be more greatly inhibited, as compared to the wild-type strain.

As described above, the characteristic, in which the Hphac1Δ strain in exponential growth phase grows more slowly in complex media containing glucose than the wild-type strain, has not been observed in the conventional yeast, which indicates that HpHac1p plays an important role in regulating gene expression for normal growth and division. Like in the conventional yeast, it was found that the growth of the Hphac1Δ strain became further inhibited under secretion stress condition such as treatment of tunicamycin or DTT, as compared to the wild-type strain.

The present inventors analyzed the differences in expression pattern of genome by microarray experiments, and the experiments were performed using the wild-type and HpHAC1 deletion strain inexponential growth phase, just before the growth pattern started to become different from each other. The genes whose expression was more reduced in the Hphac1Δ strain than in the wild-type strain are expected to be genes regulated by the transcription factor HpHac1p, which included the UPR target genes as previously classified in the conventional yeast. On the other hand, the genes whose expression was increased more in the Hphac1Δ strain than in the wild-type strain included a lot of stress response genes other than UPR target genes. This indicates that when the HpHAC1 gene relieving the secretion stress to increase secretion efficiency is deleted, cells get stressed even under the usual growth condition. Therefore, in order to relieve the stress related with secretion, other stress response genes are greatly expressed.

In still another embodiment, the present invention provides a method for developing a production host, in which the HpHAC1 gene is constantly expressed to relieve secretion stress during growth, thereby growing well.

In the present invention, UPR target genes, of which expression is directly regulated by Hphac1p, were screened by performing microarray experiments with the wild-type *H. polymorpha* and the Hphac1Δ mutant strains. Chaperone genes, which function to facilitate protein folding in the ER, and genes involved in disulfide bond formation (AAR2, ERO1, SCJ1, LHS1, PDI1), and a lot of protein families assisting glycosylation of glycoproteins are included in the gene family under the control of HpHAC1. Further, genes involved in vesicular transport between the ER and the Golgi apparatus to facilitate protein secretion (SEC66, SEC61, SEC31, SEC4, TPM1, VPS29, SEC21, SEC26, and RET2) are included.

As described above, the results of analyzing the gene family, of which expression is increased by HpHac1p, verify that the function of HpHAC1 is to increase secretory expression efficiency of *H. polymorpha*. In particular, the capacity of secretion and glycosylation of glycoprotein are improved, thus being used for preparing a production host suitable for secretory expression of glycoproteins derived from human for medical use. Accordingly, *H. polymorpha* having the improved ability of expressing and secreting recombinant proteins as a production host can be prepared by constant expression or overexpression of HpHac1p.

Examples of the recombinant proteins produced by the present invention include cytokines such as EPO, interferon-alpha, interferon-beta, interferon-gamma, and G-CSF; coagulation factors such as factor VIII, factor IX, and human protein C; therapeutic antibodies such as immunoglobulin, Fab, bispecific antibodies, single chain antibody, and diabody; Fc fusion protein; therapeutic enzymes such as glucocerebrosidase, alpha-galactosidase, alpha-L-iduronidase, and alpha-glucosidase; endothelial growth factor; growth hormone-releasing factor; *Typanosoma cruzi* trans-sialidase; HIV envelope protein; influenza virus A haemagglutinin; influenza neuraminidase; bovine enterokinase activator; bovine herpes virus type-1 glycoprotein D; human angiostatin; human B7-1, B7-2 and B-7 receptor CTLA-4; human tissue factor; growth factor (for example, platelet derived growth factor); human alpha-antitrypsin; tissue plasminogen activator; plasminogen activator inhibitor-1; urokinase; plasminogen; and thrombin.

The recombinant proteins produced by the present method can be purified by general methods known in the art, and the purification method can be selected according to the characteristics of the specific protein to be purified. Examples of the purification method include precipitation, immunoabsorption, fractionation, and various chromatographies, but are not limited thereto.

In still another embodiment, the present invention provides a method for preparing a production host, in which the HpHAC1 gene is constantly expressed or overexpressed to improve the ability of expressing and secreting recombinant proteins.

MODE FOR INVENTION

Example 1

Confirmation of HpHAC1 Splicing in *H. Polymorpha*

From the genome sequence database of *H. polymorpha*, which has been recently completed (Ramezani-Red et al., FEMS Yeast Res., 4, 207-5, 2003), a *H. polymorpha* ORF (open reading frame) showing the highest homology to the *S. cerevisiae* HAC1 gene coding for a UPR transcription factor was identified (FIG. 1A). However, the level of homology between two yeast genes was quite low (about 15%), so that several experiments were performed to confirm the estimated function of the *H. polyomorpha* homolog. In order to confirm that the *H. polymorpha* gene is an actual correspondent of the *S. cerevisiae* HAC1 gene, a reverse transcriptase-polymerase chain reaction (RT-PCR) was performed to analyze whether the *H. polymorpha* gene undergoes a non-conventional splicing event under a UPR induction condition, which is known as the most typical characteristic of ScHAC1. A *H. polymorpha* strain, DL-1 (Levine and Cooney, Appl. Microbiol., 26, 982-990, (1973)) was treated with various concentrations of DTT, which is a material that causes UPR. The cells were recovered, rapidly cooled in liquid nitrogen, and then stored at −70° C.

Further, the frozen cells were slowly thawed in ice, washed with DEPC (Diethylpyrocabohydrate)-treated water, and then RNA was isolated as follows:

750 μl of TES solution (10 mM Tris-Cl pH 7.5, 1 mM EDTA, pH 8.0, 0.5% SDS) and the same volume of acidic phenol-chloroform were added to the cells, and then heated at 65° C. for 10 minutes and vortexed for 10 seconds, followed by repeating the procedure for 1 hour. Subsequently, the cells were cooled in ice for 1 minute, vortexed for 20 seconds, and then centrifuged at 14,000 rpm and room temperature for 15 minutes. 700 μl of the supernatant was carefully transferred into a new tube, mixed well with acidic phenol-chloroform, and then centrifuged at 14,000 rpm for 5 minutes at 4° C. 600 μl of the supernatant was carefully transferred into a new tube, again. The supernatant was mixed well with the same volume of chloroform-isoamylalcohol, and then centrifuged under the same condition. Finally, the supernatant was taken, and 2.5 times volume of 100% ethanol and ¹⁄₁₀ volume of 3 M sodium acetate were added thereto, followed by vortexing for 10 seconds. The resultant was stored at −70° C. for 30 minutes (about 16 hours at −20° C.), and washed with 70% ethanol. The precipitate was dried in air. The dried precipitate was dissolved in water. The value of OD280 and OD260 was measured to quantify the RNA, and electrophoresis on a 1.2% agarose gel was performed to check its purity. 100 ug of the purified RNA was further purified using an RNeasy Mini Kit (Qiagen, USA) according to the manufacture's instruction. The concentration and purity of the final recovered RNA were determined by the value of OD280 and OD260 and gel electrophoresis in the same manners as described above.

The RT-PCR was performed using the purified RNA as a template to synthesize cDNA. Subsequently, Polymerase Chain Reaction (PCR) was performed using the obtained cDNA as a template and a pair of oligonucleotides (HpHAC1-S-for, HaHAC1-S-rev) as primers (see Table 1). The PCR product was analyzed by agarose gel electrophoresis. It was shown that two bands were detected, resulting from splicing of HpHAC1 mRNA in the sample of H. polymorpha cells treated with 5 mM DTT for 15 minutes (FIG. 1B). The diagram on right panel shows the change of HpHAC1 mRNA from an inactive form (HpHAC1u) to an active form (HpHAC1i) by splicing. The nucleic acid sequence of the obtained PCR fragment was analyzed to confirm the site of the splicing of HpHAC1 mRNA, which are underlined in FIG. 1A. It is notable that the amino acid sequence in the C-terminus of the active HpHAC1 protein was changed into a new sequence. The stop codon in the inactive form was also cleaved out by splicing, and replaced with a new subsequent stop codon.

Based on the above results, the homology between the ammo acid sequences of the spliced HpHAC1 and ScHAC1 was analyzed with software available on the web (GENE-DOC). It was revealed that the homology between two yeast HAC1 proteins is low homology with 8% identity and 15% similarity. However, it was found that the homology between the basic motif and leucine zipper domains, which are important DNA binding sites as a regulatory transcriptional factor m two proteins, is quite high with 68% identity and 77% similarity (FIG. 2)

TABLE 1

| gene | primer | Base Sequence | SEQ. ID. No. |
|---|---|---|---|
| HpHAC1 | HpHAC1-S-for | 5'-CATGAATTCGGCAATTATCGGAAGATGGC-3' | 6 |
|  | HpHAC1-S-rev | 5'-CATAAGCTTACTTGTAGATGACATGTAGTGC-3' | 7 |
| HpACT1 | HpACT1-for | 5'-TTCGATTGTCGGAAGACCTAGACA-3' | 8 |
|  | HpACT1-rev | 5'-TACCGTGCTCAATTGGGTATCTCA-3' | 9 |
| HpKAR2 | HpKAR2-for | 5'-TGCAATCATCTATGCTCTGT-3' | 10 |
|  | HpKAR2-rev | 5'-GTGGTACCAAGATCTATGCC-3' | 11 |
| HpPDI | HpPDI-for | 5'-AAGGTACCCTTTTCCTGAAT-3' | 12 |
|  | HpPDI-rev | 5'-GATCACCGGATATCCTACCA-3' | 13 |
| HpERO1 | HpERO1-for | 5'-AGAATTAACACTTTGATCGG-3' | 14 |
|  | HpERO1-rev | 5'-TGTTCTCGAACTGATGGAAG-3' | 15 |
| HpHAC1-N | HpHAC1-N-for | 5'-CCTAAACACGCACGCCTCACAGCTGTTGAGAGCAGTCAT-3' | 16 |
|  | HpHAC1-N-rev | 5'-GCACAGTGTTGTATCAAACG-3' | 17 |
| HpHAC1-C | HpHAC1-C-for | 5'-CCAACGGTAAGAAATTCAAG-3' | 18 |
|  | HpHAC1-C-rev | 5'-CGTATTACCAAACCGCTTACGTACGCTCTTTTAATAGCGTGCAT-3' | 19 |
| Leu-N | LeuN-for | 5'-GTACGTAAGCGGTTTGGTAATACG-3' | 20 |
|  | LeuN-rev | 5'-CAAACATGTTGTTGGTGACA-3' | 21 |
| Leu-C | LeuC-for | 5'-TTGGTGGAATCTACTTTGGT-3' | 22 |
|  | LeuC-rev | 5'-GTGAGGCGTGCGTGTTTAGG-3' | 23 |
| HpHAC1s | HpHAC1s-for | 5'-CCGGAATTCATGACTGCTCTCAACAGCTC-3' | 24 |
|  | HpHAC1s-rev | 5'-CCCAAGCTTTCACGCATAGTCAGGAACATCGTATGGGTAAGACAAATAGTCGTCAAATTC-3' | 25 |

Example 2

Exploration of Conditions for Inducing UPR (Unfold Protein Response) in Hansenula Polymorpha To check whether UPR was induced, the splicing of HpHAC1 mRNA (FIG. 3A) and the increased expression level of the conventional UPR target genes (FIG. 3B) were examined using RT-PCR. The A16 strain derived from H. polymorpha CBS 4732 was treated with stress-inducing agents, such as tunicamycin, DTT (Dithiothreitol), and Blefeldin A, in order to induce various secretion stresses including glycosylation inhibition, reduction stress, and inhibition of protein transport in the ER, respectively. The optimal concentrations of the stress-inducing agents to induce UPR in the treated cells were examined.

First, in order to cultivate yeast cells, YPD (yeast extract 1%, bacto peptone 2%, and glucose 2%) medium containing glucose as a main carbon source was used. The cells were cultured in 3 ml of YPD medium at 170 rpm, 37° C. for 16 hours, and inoculated in 50 ml of YPD medium to be an OD600 of 0.1. When OD600 of the cells reached around 0.3 to 0.4, the cells were recovered. The cells were equally resuspended in YPD only and YPD containing various concentrations of tunicamycin, DTT, and Blefeldin A at pH 5.4, and then cultured under the same conditions. At the time points of 30 minutes, 1 hour, and 2 hours after culture, yeast cells were recovered and determined for OD600. Subsequently, the RNA extraction, purification, and RT-PCR were performed as described in Example 1. For the confirmation of HpHAC1 mRNA splicing, the primers HpHAC1-S-for and HaHAC1-S-rev (Table 1) were used. The expression level of the conventional UPR target genes was confirmed by PCR using the primer sets described in Table 2.

From the results of examining the splicing of HpHAC1 mRNA in the samples treated with various concentrations of tunicamycin, DTT, and Blefeldin A, the suitable splicing patterns in HpHAC1 were found to be shown at the concentration of 5 ug/ml tunicamycin, 5 mM DTT, and 5 µg/ml Blefeldin A. The time course experiments showed that the splicing patterns in each sample treated with tunicamycin and Blefeldin A, inhibiting glycosylation of secretory protein or inhibiting protein transport from ER, respectively, are different from that in the sample treated with DTT, which inhibits a disulfide bond to induce ER stress. In the samples treated with tunicamycin and Blefeldin A, the splicing extent was increased with the incubation time. Meanwhile, in the sample treated with DTT, it was found that the splicing was occurred to a less extent with the maximum value at 30 minutes, and then decreased after then (FIG. 3A).

A semi-quantitative RT-PCR was performed using the *H. polymorpha* genes (HpKAR2, HpPDI1, HpERO1) corresponding to the *S. cerevisiae* UPR target genes, ScKAR2, ScPDI1, and ScERO1, whose expression levels were shown to be increased by UPR in the conventional yeast. As a control for comparison, the RT-PCR for HpACT1 was performed under the same conditions. As a result, it was found that the expression levels of HpKAR2, HpERO1, and HpPDI1 were increased by ER stress.

Example 3

Construction and Characterization of the HpHAC1 Gene Deletion and Overexpression Strains In order to construct a *H. polymorpha* HpHAC1 deletion mutant, the HpHAC1 gene was deleted using fusion PCR and in vivo DNA recombination (Oldenburg et al., Nucleic Acid Res., 25, 451, 1997).

In the primary PCR, four pairs of primers described in Table 1 were used to amplify each N-terminus and C-terminus of LEU2 gene (N-terminus; LeuN-for, LeuN-rev, C-terminus; LeuC-for, LeuC-rev) and HpHAC1 gene (N-terminus; HpHAC1-N-for, HpHAC1-N-rev, C-terminus; HpHAC1-C-for, HpHAC1-C-rev). Then, in the secondary fusion PCR, two pairs of primers were used to link the N-terminus of HpHAC1 gene and the N-terminus of LEU2 gene (HpHAC1-N-for, LeuN-rev), and the C-terminus of LEU2 gene and the C-terminus of HpHAC1 gene (LeuC-for, HpHAC1-C-rev). Each obtained DNA fragments were introduced into yeast cells, and the transformants with the HpHAC1 gene deletion by in vivo DNA recombination were screened (FIG. 4). First, LEU2+ transformants grown in minimal media lacking Leucine were selected, and PCR was performed to select the *H. polymorpha* mutant strain with the HpHAC1 gene deletion (Hphac1Δ (hac1::LEU2)), the by comparing the amplified DNA fragments of HpHAC1 of the obtained transformants with the one of wild type. In order to construct a *H. polymorpha* mutant strain, in which the HpHAC1 gene is overexpressed, the HpHAC1 overexpression vector was prepared as followings. PCR was performed using the cDNA obtained in Example 1 as a template and the oligonucleotide set (HpHAC1s_for and HpHAC1s_rev) as primers (Table 1) to amplify the DNA fragment of HpHAC1, which was treated with restriction enzymes EcoRI and HindIII, and then ligated to the EcoRI/HindIII-treated pGAP vector containing the HpLEU2 gene as a selection marker and HARS (FIG. 6). The resultant recombinant vector pGAP-HpHAC1s containing the cDNA fragment corresponding to the spliced HpHAC1 mRNA was screened by PCR and sequencing analysis. Subsequently, the obtained vector was introduced into *H. polymorpha* cells, and the LEU2+ transformants grown in the minimal media lacking Leucine were selected. Chromosomal DNA was extracted from the transformants for analysis of the presence of pGAP-HpHAC1s. As a result, a transformant DL1-H1s strain, in which extra copies of the HpHAC1 gene were introduced for overexpression, was finally developed.

Example 4

Gene Expression Profiling of *H. Polymorpha* Wild-Type and HpHAC1 Deletion Strains As mentioned in Example 3, in order to investigate the reason why the HpHAC1 deletion strain grows more slowly than the wild-type, a DNA microarray analysis as the most representative functional genomics approach was performed. A DL1L stain, a derivative of *H. polymorpha* DL1 strain in which the LEU gene was introduced, was used as a wild-type strain, and the strain constructed in Example 3 was used as an HpHAC1 deletion strain (Hphac1Δ). Two strains were cultured in YPD complex media containing glucose as a main carbon source, and each strain was recovered in exponential growth phase. RNA was isolated and purified from each *H. polymorpha* strain, and the difference in the global gene expression profiles between two strains was analyzed using a DNA microarray (FIG. 3).

The experimental method will be described in more detail as follows: The *H. polymorpha* DL1L and Hphac1Δ strains were seed-cultured in 3 ml of YPD media at 170 rpm and 37° C. for 16 hours, and then the yeast cells were inoculated in 50 ml of YPD media to be an OD600 of 0.1. The inoculated cells were cultured under the same conditions, and recovered at the point of OD600 of 0.5, which corresponded the exponential growth phase before growth differences were observed. Total RNA was isolated and purified from the recovered cells in the same manners as described in Example 1.

All the experiments for cDNA preparation, hybridization, and fluorescence labeling were performed using a 3DNA™ Submicro Expression Array Detection kit (Genisphere Co.) according to the manufacture's instruction. Briefly, 70 µg of total RNA were used for cDNA synthesis, and the RT primers provided in the kit were added to react at 80° C. for 10 minutes. The reacted RNA was cooled in ice, and an RNase Inhibitor, Superase-In™, a RT buffer, a dNTP mixture, and a reverse transcriptase mixture were added thereto. The reaction was performed at 42° C. for 2 hours, and 3.5 ul of 0.5 M NaOH/50 mM EDTA solution was added thereto to stop the reaction. To denature DNA/RNA hybrids, the reactant was incubated at 65° C. for 20 minutes, and neutralized with a 1 M Tris-HCl buffer solution (pH 7.5). The obtained cDNA reactant was purified and concentrated using a PCR purification kit (Qiagen Co.), and a hybridization buffer and a LNA dT blocker were added thereto to react at 80° C. for 10 minutes and then 50° C. for 20 minutes. Subsequently, the reacted cDNA was dropped on an array slide, and hybridized in the dark at 45° C. for 18 hours. The slide was washed with 2×SSC/0.1% SDS, 2×SSC, 0.2×SSC, and distilled water, and then completely dried. Next, a fluorescent molecule, 3DNA capture reagent and a hybridization buffer solution were mixed to react at 80° C. for 10 minutes, and at 50° C. for 20 minutes. The reactant was dropped on the above slide, and hybridized in the dark at 50° C. for 6 hours. Then the slide was washed in the same process as described above, so as to generate a final microarray slide to observe.

The microarray slides were scanned with a ScanArray 5000, and image files were obtained. Further, the image processing, which consists of three steps of spot finding, quantification, and background estimation, was performed using a GenePix 4.0 program (Axon) for data normalization. The differences in expression were also analyzed using the same program. The result of transcriptome profile analysis of the wild-type and Hphac1Δ strains in exponential growth phase showed apparent differences in the expression patterns of various genes, despite that they were captured before the growth difference was observed (FIG. 7B). The *H. polymorpha* genes, of which expression was significantly decreased in the Hphac1Δ strain than in the wild-type strain, are expected to be the genes involved in UPR controlled by the regulatory transcription factor HpHac1p, and mainly include the genes corresponding to UPR target genes as identified in the conventional yeast *S. cerevisiae* (Table 2). More specifically, the deletion of HpHAC1 was found to decrease the expression of several groups of genes, such as ERG chaperone genes, which function to facilitate protein folding in the ER, (KAR2, ERO1, SCJ1, LHS1), genes involved in glycosylation of glycoprotein (OST1, OST4, SYP1, WBP1, STT3, MNN2, MNN9, KTR1, KTR4, PMI40, PMT2, PMT5), and genes involved in protein secretion (ERV41, VIP36, SEC53, YSY6, EMP79).

TABLE 2

| Function | Gene whose expression is decreased |
| --- | --- |
| Protein folding | KAR2, ERO1, SCJ1, LHS1, HAC1 |
| Glycosylation | OST1, OST4, STT3, WBP1, SWP1, PMT2, PMT5, PMT40, MNN2, MNN9, KTR1, KTR4 |
| Secretion | ERV41, VIP36, SEC53, YSY6, EMP70 |
| Protein degradation | CPS1, asparaginase amidase N, YBR139W |

The genes, of which expression was increased more in the Hphac1Δ strain than in the wild-type strain, was found to be the genes encoding heat shock proteins (HSPs) involved in the recovery from stress such as HSP26, HSP78, HSP12, HSP10, HSP42, HSP104, HSP60, DDR48, SIT1, STI1, SIS1, and HSC82, the genes involved in the removal of free radicals to induce DNA and protein damages in vivo (SKN7, SOD2, HYR1), the genes facilitating protein folding (MTL1, MDJ1, DNAJ, CRP6), the genes involved in degradation of misfolded proteins (PRB1, BUL1, CDC48, HUL5), and the genes involved in the synthesis of trehalose protecting biological structures (TPS1, TPS53) (Table 3). These results indicate that the deletion of HpHAC1 gene, which codes for the positive transcription factor for those genes involved in relieving secretion stress, leads to more induced expression of other stress relief genes, not being regulated by the Hphac1 protein, to alleviate the secretion stress. Namely, it can be explained that several gene families involved in secretion stress relief cannot function properly due to the HpHAC1 deletion, whereby the expression of other stress relief genes were increased, as a kind of compensation reaction.

TABLE 3

| Function | Gene whose expression is increased |
| --- | --- |
| Stress response | HSP26, HSP78, HSP12, HSP10, HSP42, HSP104, HSP60, DDR48, SIT1, STI1, SIS1, HSC82 |

TABLE 3-continued

| Function | Gene whose expression is increased |
| --- | --- |
| Oxydation stress | SKN7, SOD2, HYR1 |
| Trehalose | TPS1, TPS3 |
| Protein degradation | PRB1, BUL1, CDC48, HUL5 |
| Protien folding | MTL1, MDJ1, DNA, CRP6 |
| Cell wall | DNA4, ECM13, BGL2, GSC2, WSC4, CCW1, CRH1 |
| Signaling | MSG5, CMK1 |
| Transport | SIT1, ITR1, AGP2, PMC1, ENB1, TNA1 |

Example 5

Screening of UPR Target Genes Regulated by HpHac1 Protein

To screen the UPR target genes regulated by HpHac1p, two sets of microarray analysis were performed. First, the wild-type strain was cultured until the exponential growth phase, and divided into two groups. One group was treated with tunicamycin or DTT, and then continuously cultured. The other group was cultured without any treatment as a control. The cells of two groups were recovered at the time point of 30 minutes, 60 minutes, and 120 minutes after the treatment, and then microarray analysis was performed as described in Example 4 (left in FIG. 8A). For the second microarray analysis, the wild-type and Hphac1Δ strains were cultured until the exponential growth phase. Then, the cells of two strains were treated with tunicamycin or DTT, and recovered at the time point of 30 minutes, 60 minutes, and 120 minutes after the treatment. Microarray analysis was performed for the recovered cells (right in FIG. 8A).

In the first microarray analysis, all of the genes whose expressions were increased with the treatment of tunicamycin or DTT were screened, so that a gene family, which responds to secretion or secretion-related stress, could be selected. In the second microarray analysis, the differences in expression pattern between the wild-type and Hphac1Δ strains were analyzed under secretion stress condition, in order to screen the UPR target genes directly regulated by HpHac1p. Therefore, the genes whose expression was increased depending on HpHac1p in the second microarray analysis were screened to exist in the gene lists selected in the first microarray analysis, so that indirect effects generated by the HpHAC1 deletion could be removed. Further, in both of the microarray analyses, the cells had undergone the secretion stress induced by either DTT or tunicamycin treatment, which inhibits disulfide bond formation or glycosylation of protein, respectively, and only the genes whose expressions were increased under both secretion stresses were screened to remove the possible side effect generated from each reaction.

Based on the tight screening criteria as described above, the screened UPR target genes under the control of HpHac1p are shown in Table 4. The screened genes mainly include several gene families having specific functions. Specifically, the chaperone genes, which function to facilitate protein folding in ER, and the genes involved in disulfide bond formation (KAR2, ERO1, SCJ1, LHS1, PDI1), and the genes involved in glycosylation of glycoprotein (ALG5, OPU24, OST1, OST2, OST4, SWP1, WBP1, KTR1, OCR5, GPI17, MNN4, MNN10, KTR4) are included as the HpHAC1 regulons (FIG. 8B). Further, the expression of the genes involved in transport of secretory proteins from the ER to the Golgi apparatus (SEC66, SEC61, SEC31, SEC4, TMP1, VPS29) and the genes involved in reverse-transport of vesicles from the Golgi apparatus to the ER (SEC21, SEC26, RET2) were notably dependent on the presence of HpHAC1p.

TABLE 4

| Function | Gene regulated by HpHAC1 |
|---|---|
| Translocation | SEC66, SEC61 |
| Glycosylation/modification | |
| Core oligosacchride synthesis | ALG5, GPI17, OPU24 |
| Oligosacchryltransferase | OST1, OST2, OST4, SWP1, WBP1 |
| Golgi/O-linked glycosylation | KTR4, KTR1, MNN2, MNN4, MNN10, OCR5, |
| Protein folding | |
| Chaperones | LHS1, SCJ1, KAR2 |
| Disulfide bond formation | ERO1, PDI1 |
| Protein degradation | asparaginase amidase N, CUE1 |
| Vesicle trafficking/Transport | |
| Budding (ER-Golgi) | SEC31, SEC4, TPM1, VPS29 |
| Retrieval (Golgi-ER) | SEC21, SEC26, RET2 |
| Cell wall biosynthesis | DCW1 |
| Cytoskeleton | ARC35, CAP2, ARP2, SLA2, ARC19, ARC15, PAN1 |

INDUSTRIAL APPLICABILITY

In the present invention, the HpHAC1 gene for a key regulatory factor of Unfolded Protein Response in *H. polymorpha* and its spliced form of HpHAC1 mRNA capable of encoding the active HpHAC1 protein were identified, and their nucleic acid sequences were also identified. Further, in the invention, the UPR target genes whose expression is regulated by the HpHac1 protein were identified by microarray analysis.

According to the present invention, a method for improving the ability of secretory expression and growth of *H. polymorpha* can be provided by constant expression or overexpression of the HpHAC1 protein.

Further, according to the present invention, *H. polymorpha* having the improved ability of secretory expression and growth can be developed as a production host. The secretory expression system of *H. polymorpha* developed by the present invention can be used for the mass-production of secretory proteins for industrial and medical applications, thereby producing a large amount of the proteins at low cost. Accordingly, the method is employed in the production of recombinant proteins for industrial and medical use, so as to reduce economic burden for a patient, and contribute to the improvement in the welfare of all humankind.

The invention claimed is:

1. An isolated protein having the amino acid sequence of SEQ ID NO: 3.

2. An isolated nucleic acid encoding a protein having the amino acid sequence of SEQ ID NO:3.

3. The isolated nucleic acid according to claim 2, having the nucleotide sequence of SEQ ID NO: 1 or 2.

4. A recombinant vector comprising the isolated nucleic acid of claim 2.

5. A recombinant vector comprising the isolated nucleic acid of claim 3.

6. The recombinant vector according to claim 4, having the deposit number of Korean Collection for Type Cultures (KCTC) 10960BP.

7. A *Hansenula polymorpha* transformant transformed by the recombinant vector of claim 4.

8. An isolated nucleic acid comprising the nucleotide sequence of SEQ ID NO: 2.

9. A method for producing a recombinant protein, comprising the steps of further transforming the *Hansenula polymorpha* transformant of claim 7 with a polynucleotide encoding a recombinant protein; and culturing the resulting transformant to produce the recombinant protein.

* * * * *

SEQUENCE LISTING

```
<160> NUMBER OF SEQ ID NOS: 25

<210> SEQ ID NO 1
<211> LENGTH: 1197
<212> TYPE: DNA
<213> ORGANISM: Artificial Sequence
<220> FEATURE:
<223> OTHER INFORMATION: Synthetic

<400> SEQUENCE: 1
atgactgctc tcaacagctc tgtccagcac caagaagtct cttcggactt gcctttgga      60 actctacctc caagaaagcg tgccaagacc gaagaggaga aagagcaaag aagagttgaa     120
agaatcttga aaacagaag ggcagctcac gcgtctagag aaaagaagag aagacatgtt     180
gagtacctgg aaaactatgt gactgatctg gagtctgcgc tggcgacaca tgagggcaat    240
tatcggaaga tggccaaaat tcaatcgagc ctgatatctc tgttgtctga acatggaatc    300
gattactcgt ctgtggattt agctgttgaa ccatgtccta aagttgaaag accggaaggt    360
ttggagttga ctggttcaat tccagtgaaa aaacagaaaa tcgcctcggc gaaatcgccc    420
aaatcgttat cgagaaaatc gaagtcggaa atcccatcac caagttttga tgagaatatt    480
ttttctgagg aggaaaacga acatgacgat ggtattgagg aatacgggaa agcaggacaa    540
gaagcaaccg aggctccatc cttgtctcac aaccgcaaaa gaaggcgca agatgcttat     600 atctcgcctc cgggctccac ctccccatcc aagttgaaac ttgaagaaga cgaaaggatc    660
tccaaacatg aatacagtaa cttgtttgat gacaccgatg acattttccc gtcggagaag    720
tcatcaagtc tcgagctgta taaacaggat gatctgacca tggcatcatt tgtgaaacaa    780
gaagaggaag aaatggtgcc atttgtgaaa caggaagacg agttcaagtt tcctgattcg    840
ggtttcaacg ctgacgattg tcatcttatc caagtggaag acctctgctc ttttaatagc    900
gtgcatcatc cagcagtgat gattgtaaag ttatgaaaga ctcaaatgtt tgaagcgatt    960
cagtggaagc aacttgaaat gagactggtt ttttgggtat ttgtttgaca gtctcatctc   1020
aagtatgggt atgagttatt tggttatctt gtgctctgct tctactcgct ttaattgtta   1080
```

```
agttggtcag cagcaccatt aacagcagag agtatcgaca accactttga atttgcagca    1140
ccattaacag cagagagtat cgacaaccac tttgaatttg acgactattt gtcttga      1197
```

<210> SEQ ID NO 2
<211> LENGTH: 978
<212> TYPE: DNA
<213> ORGANISM: Artificial Sequence
<220> FEATURE:
<223> OTHER INFORMATION: Synthetic

<400> SEQUENCE: 2

```
atgactgctc tcaacagctc tgtccagcac caagaagtct cttcggactt gccttttgga     60
actctacctc caagaaagcg tgccaagacc gaagaggaga aagagcaaag aagagttgaa    120
agaatcttga gaaacagaag ggcagctcac gcgtctagag aaaagaagag aagacatgtt    180
gagtacctgg aaaactatgt gactgatctg gagtctgcgc tggcgacaca tgagggcaat    240
tatcggaaga tggccaaaat tcaatcgagc ctgatatctc tgttgtctga acatggaatc    300
gattactcgt ctgtggattt agctgttgaa ccatgtccta agttgaaaag accggaaggt    360
ttggagttga ctggttcaat tccagtgaaa aaacagaaaa tcgcctcggc gaaatcgccc    420
aaatcgttat cgagaaaatc gaagtcggaa atcccatcac caagttttga tgagaatatt    480
ttttctgagg aggaaaacga acatgacgat ggtattgagg aatacgggaa agcaggacaa    540
gaagcaaccg aggctccatc cttgtctcac aaccgcaaaa gaaaggcgca agatgcttat    600
atctcgcctc cgggctccac ctccccatcc aagttgaaac ttgaagaaga cgaaaggatc    660
tccaaacatg aatacagtaa cttgtttgat gacaccgatg acatttttccc gtcggagaag    720 tcatcaagtc tcgagctgta taaacaggat gatctgacca tggcatcatt tgtgaaacaa    780
gaagaggaag aaatggtgcc atttgtgaaa caggaagacg agttcaagtt tcctgattcg    840
ggtttcaacg ctgacgattg tcatcttatc caagtggaag acctctgctc ttttaatagc    900
gtgcatcatc cagcagcagc accattaaca gcagagagta tcgacaacca ctttgaattt    960
gacgactatt tgtcttga                                                 978
```

<210> SEQ ID NO 3
<211> LENGTH: 325
<212> TYPE: PRT
<213> ORGANISM: Artificial Sequence
<220> FEATURE:
<223> OTHER INFORMATION: Synthetic

<400> SEQUENCE: 3

```
Met Thr Ala Leu Asn Ser Ser Val Gln His Gln Glu Val Ser Asp
1               5                   10                  15

Leu Pro Phe Gly Thr Leu Pro Pro Arg Lys Arg Ala Lys Thr Glu Glu
            20                  25                  30

Glu Lys Glu Gln Arg Arg Val Glu Arg Ile Leu Arg Asn Arg Ala
35                  40                  45

Ala His Ala Ser Arg Glu Lys Lys Arg Arg His Val Glu Tyr Leu Glu
    50                  55                  60

Asn Tyr Val Thr Asp Leu Glu Ser Ala Leu Ala Thr His Glu Gly Asn
65                  70                  75                  80

Tyr Arg Lys Met Ala Lys Ile Gln Ser Ser Leu Ile Ser Leu Leu Ser
                85                  90                  95

Glu His Gly Ile Asp Tyr Ser Ser Val Asp Leu Ala Val Glu Pro Cys
            100                 105                 110
```

-continued

```
Pro Lys Val Glu Arg Pro Glu Gly Leu Glu Leu Thr Gly Ser Ile Pro
            115                 120                 125
Val Lys Lys Gln Lys Ile Ala Ser Ala Lys Ser Pro Lys Ser Leu Ser
        130                 135                 140
Arg Lys Ser Lys Ser Glu Ile Pro Ser Pro Ser Phe Asp Glu Asn Ile
145                 150                 155                 160
Phe Ser Glu Glu Asn Glu His Asp Asp Gly Ile Glu Glu Tyr Gly
                165                 170                 175
Lys Ala Gly Gln Glu Ala Thr Glu Ala Pro Ser Leu Ser His Asn Arg
            180                 185                 190
Lys Arg Lys Ala Gln Asp Ala Tyr Ile Ser Pro Pro Gly Ser Thr Ser
        195                 200                 205
Pro Ser Lys Leu Lys Leu Glu Glu Asp Glu Arg Ile Ser Lys His Glu
    210                 215                 220
Tyr Ser Asn Leu Phe Asp Asp Thr Asp Ile Phe Pro Ser Glu Lys
225                 230                 235                 240
Ser Ser Ser Leu Glu Leu Tyr Lys Gln Asp Leu Thr Met Ala Ser
                245                 250                 255
Phe Val Lys Gln Glu Glu Glu Met Val Pro Phe Val Lys Gln Glu
            260                 265                 270
Asp Glu Phe Lys Phe Pro Asp Ser Gly Phe Asn Ala Asp Asp Cys His
        275                 280                 285
Leu Ile Gln Val Glu Asp Leu Cys Ser Phe Asn Ser Val His His Pro
    290                 295                 300
Ala Ala Ala Pro Leu Thr Ala Glu Ser Ile Asp Asn His Phe Glu Phe
305                 310                 315                 320
Asp Asp Tyr Leu Ser
                325
```

<210> SEQ ID NO 4
<211> LENGTH: 311
<212> TYPE: PRT
<213> ORGANISM: Artificial Sequence
<220> FEATURE:
<223> OTHER INFORMATION: Synthetic

<400> SEQUENCE: 4

```
Met Thr Ala Leu Asn Ser Ser Val Gln His Gln Glu Val Ser Ser Asp
1               5                   10                  15
Leu Pro Phe Gly Thr Leu Pro Pro Arg Lys Arg Ala Lys Thr Glu Glu
            20                  25                  30
Glu Lys Glu Gln Arg Arg Val Glu Arg Ile Leu Arg Asn Arg Arg Ala
        35                  40                  45
Ala His Ala Ser Arg Glu Lys Lys Arg Arg His Val Glu Tyr Leu Glu
    50                  55                  60
Asn Tyr Val Thr Asp Leu Glu Ser Ala Leu Ala Thr His Glu Gly Asn
65                  70                  75                  80
Tyr Arg Lys Met Ala Lys Ile Gln Ser Ser Leu Ile Ser Leu Leu Ser
                85                  90                  95
Glu His Gly Ile Asp Tyr Ser Ser Val Asp Leu Ala Val Glu Pro Cys
            100                 105                 110
Pro Lys Val Glu Arg Pro Glu Gly Leu Glu Leu Thr Gly Ser Ile Pro
        115                 120                 125
Val Lys Lys Gln Lys Ile Ala Ser Ala Lys Ser Pro Lys Ser Leu Ser
    130                 135                 140
Arg Lys Ser Lys Ser Glu Ile Pro Ser Pro Ser Phe Asp Glu Asn Ile
```

```
                145                 150                 155                 160
Phe Ser Glu Glu Glu Asn Glu His Asp Asp Gly Ile Glu Glu Tyr Gly
                    165                 170                 175

Lys Ala Gly Gln Glu Ala Thr Glu Ala Pro Ser Leu Ser His Asn Arg
                180                 185                 190

Lys Arg Lys Ala Gln Asp Ala Tyr Ile Ser Pro Pro Gly Ser Thr Ser
            195                 200                 205

Pro Ser Lys Leu Lys Leu Glu Glu Asp Glu Arg Ile Ser Lys His Glu
        210                 215                 220

Tyr Ser Asn Leu Phe Asp Asp Thr Asp Asp Ile Phe Pro Ser Glu Lys
225                 230                 235                 240

Ser Ser Ser Leu Glu Leu Tyr Lys Gln Asp Asp Leu Thr Met Ala Ser
                245                 250                 255

Phe Val Lys Gln Glu Glu Glu Met Val Pro Phe Val Lys Gln Glu
                260                 265                 270

Asp Glu Phe Lys Phe Pro Asp Ser Gly Phe Asn Ala Asp Asp Cys His
                275                 280                 285

Leu Ile Gln Val Glu Asp Leu Cys Ser Phe Asn Ser Val His His Pro
            290                 295                 300

Ala Val Asn Ile Val Lys Leu
305                 310

<210> SEQ ID NO 5
<211> LENGTH: 236
<212> TYPE: PRT
<213> ORGANISM: Artificial Sequence
<220> FEATURE:
<223> OTHER INFORMATION: Synthetic

<400> SEQUENCE: 5

Met Glu Met Thr Asp Phe Glu Leu Thr Ser Asn Ser Gln Ser Asn Leu
1               5                   10                  15

Ala Ile Pro Thr Asn Phe Lys Ser Thr Leu Pro Pro Arg Lys Arg Ala
                20                  25                  30

Lys Thr Lys Glu Glu Lys Glu Gln Arg Arg Ile Glu Arg Ile Leu Arg
            35                  40                  45

Asn Arg Arg Ala Ala His Gln Ser Arg Glu Lys Lys Arg Leu His Leu
        50                  55                  60

Gln Tyr Leu Glu Arg Lys Cys Ser Leu Leu Glu Asn Leu Leu Asn Ser
65                  70                  75                  80

Val Asn Leu Glu Lys Leu Ala Asp His Glu Asp Ala Leu Thr Cys Ser
                85                  90                  95

His Asp Ala Phe Val Ala Ser Leu Asp Glu Tyr Arg Asp Phe Gln Ser
                100                 105                 110

Thr Arg Gly Ala Ser Leu Asp Thr Arg Ala Ser Ser His Ser Ser Ser
            115                 120                 125

Asp Thr Phe Thr Pro Ser Pro Leu Asn Cys Thr Met Glu Pro Ala Thr
        130                 135                 140

Leu Ser Pro Lys Ser Met Arg Asp Ser Ala Ser Asp Gln Glu Thr Ser
145                 150                 155                 160

Trp Glu Leu Gln Met Phe Lys Thr Glu Asn Val Pro Glu Ser Thr Thr
                165                 170                 175

Leu Pro Ala Val Asp Asn Asn Asn Leu Phe Asp Ala Val Ala Ser Pro
            180                 185                 190

Leu Ala Asp Pro Leu Cys Asp Asp Ile Ala Gly Asn Ser Leu Pro Phe
        195                 200                 205
```

Asp Asn Ser Ile Asp Leu Asp Asn Trp Arg Asn Pro Glu Arg Ser Gln
    210                 215                 220

Val Ile His Leu Asn Met Ile Ser Ser Ser Leu His
225                 230                 235

```
<210> SEQ ID NO 6
<211> LENGTH: 29
<212> TYPE: DNA
<213> ORGANISM: Artificial Sequence
<220> FEATURE:
<223> OTHER INFORMATION: Synthetic

<400> SEQUENCE: 6
catgaattcg gcaattatcg gaagatggc                                    29

<210> SEQ ID NO 7
<211> LENGTH: 31
<212> TYPE: DNA
<213> ORGANISM: Artificial Sequence
<220> FEATURE:
<223> OTHER INFORMATION: Synthetic

<400> SEQUENCE: 7
cataagctta cttgtagatg acatgtagtg c                                 31

<210> SEQ ID NO 8
<211> LENGTH: 24
<212> TYPE: DNA
<213> ORGANISM: Artificial Sequence
<220> FEATURE:
<223> OTHER INFORMATION: Synthetic

<400> SEQUENCE: 8
ttcgattgtc ggaagaccta gaca                                         24

<210> SEQ ID NO 9
<211> LENGTH: 24
<212> TYPE: DNA
<213> ORGANISM: Artificial Sequence
<220> FEATURE:
<223> OTHER INFORMATION: Synthetic

<400> SEQUENCE: 9
taccgtgctc aattgggtat ctca                                         24

<210> SEQ ID NO 10
<211> LENGTH: 20
<212> TYPE: DNA
<213> ORGANISM: Artificial Sequence
<220> FEATURE:
<223> OTHER INFORMATION: Synthetic

<400> SEQUENCE: 10
tgcaatcatc tatgctctgt                                              20

<210> SEQ ID NO 11
<211> LENGTH: 20
<212> TYPE: DNA
<213> ORGANISM: Artificial Sequence
<220> FEATURE:
<223> OTHER INFORMATION: Synthetic

<400> SEQUENCE: 11
gtggtaccaa gatctatgcc                                              20
```

```
<210> SEQ ID NO 12
<211> LENGTH: 20
<212> TYPE: DNA
<213> ORGANISM: Artificial Sequence
<220> FEATURE:
<223> OTHER INFORMATION: Synthetic

<400> SEQUENCE: 12
aaggtaccct tttcctgaat                                                 20

<210> SEQ ID NO 13
<211> LENGTH: 20
<212> TYPE: DNA
<213> ORGANISM: Artificial Sequence
<220> FEATURE:
<223> OTHER INFORMATION: Synthetic

<400> SEQUENCE: 13
gatcaccgga tatcctacca                                                 20

<210> SEQ ID NO 14
<211> LENGTH: 20
<212> TYPE: DNA
<213> ORGANISM: Artificial Sequence
<220> FEATURE:
<223> OTHER INFORMATION: Synthetic

<400> SEQUENCE: 14
agaattaaca ctttgatcgg                                                 20

<210> SEQ ID NO 15
<211> LENGTH: 20
<212> TYPE: DNA
<213> ORGANISM: Artificial Sequence
<220> FEATURE:
<223> OTHER INFORMATION: Synthetic

<400> SEQUENCE: 15
tgttctcgaa ctgatggaag                                                 20

<210> SEQ ID NO 16
<211> LENGTH: 39
<212> TYPE: DNA
<213> ORGANISM: Artificial Sequence
<220> FEATURE:
<223> OTHER INFORMATION: Synthetic

<400> SEQUENCE: 16
cctaaacacg cacgcctcac agctgttgag agcagtcat                            39

<210> SEQ ID NO 17
<211> LENGTH: 20
<212> TYPE: DNA
<213> ORGANISM: Artificial Sequence
<220> FEATURE:
<223> OTHER INFORMATION: Synthetic

<400> SEQUENCE: 17
gcacagtgtt gtatcaaacg                                                 20

<210> SEQ ID NO 18
<211> LENGTH: 20
<212> TYPE: DNA
<213> ORGANISM: Artificial Sequence
<220> FEATURE:
<223> OTHER INFORMATION: Synthetic

<400> SEQUENCE: 18
```
ccaacggtaa gaaattcaag                                               20

<210> SEQ ID NO 19
<211> LENGTH: 44
<212> TYPE: DNA
<213> ORGANISM: Artificial Sequence
<220> FEATURE:
<223> OTHER INFORMATION: Synthetic

<400> SEQUENCE: 19
cgtattacca aaccgcttac gtacgctctt ttaatagcgt gcat                    44

<210> SEQ ID NO 20
<211> LENGTH: 24
<212> TYPE: DNA
<213> ORGANISM: Artificial Sequence
<220> FEATURE:
<223> OTHER INFORMATION: Synthetic

<400> SEQUENCE: 20
gtacgtaagc ggtttggtaa tacg                                          24

<210> SEQ ID NO 21
<211> LENGTH: 20
<212> TYPE: DNA
<213> ORGANISM: Artificial Sequence
<220> FEATURE:
<223> OTHER INFORMATION: Synthetic

<400> SEQUENCE: 21
caaacatgtt gttggtgaca                                               20

<210> SEQ ID NO 22
<211> LENGTH: 20
<212> TYPE: DNA
<213> ORGANISM: Artificial Sequence
<220> FEATURE:
<223> OTHER INFORMATION: Synthetic

<400> SEQUENCE: 22
ttggtggaat ctactttggt                                               20

<210> SEQ ID NO 23
<211> LENGTH: 20
<212> TYPE: DNA
<213> ORGANISM: Artificial Sequence
<220> FEATURE:
<223> OTHER INFORMATION: Synthetic

<400> SEQUENCE: 23
gtgaggcgtg cgtgtttagg                                               20

<210> SEQ ID NO 24
<211> LENGTH: 29
<212> TYPE: DNA
<213> ORGANISM: Artificial Sequence
<220> FEATURE:
<223> OTHER INFORMATION: Synthetic

<400> SEQUENCE: 24
ccggaattca tgactgctct caacagctc                                     29

<210> SEQ ID NO 25
<211> LENGTH: 60
<212> TYPE: DNA
<213> ORGANISM: Artificial Sequence -continued

```
<220> FEATURE:
<223> OTHER INFORMATION: Synthetic

<400> SEQUENCE: 25
cccaagcttt cacgcatagt caggaacatc gtatgggtaa gacaaatagt cgtcaaattc    60
```